(12) United States Patent
Green

(10) Patent No.: US 9,072,800 B2
(45) Date of Patent: Jul. 7, 2015

(54) HAND SANITIZER

(75) Inventor: Bruce Philip Green, Northampton (GB)

(73) Assignee: TRISTEL PLC, Snailwell, Newmarket (GB)

( * ) Notice: Subject to any disclaimer, the term of this patent is extended or adjusted under 35 U.S.C. 154(b) by 0 days.

(21) Appl. No.: 13/321,403

(22) PCT Filed: Mar. 29, 2010

(86) PCT No.: PCT/GB2010/050525
§ 371 (c)(1),
(2), (4) Date: Jan. 30, 2012

(87) PCT Pub. No.: WO2010/133855
PCT Pub. Date: Nov. 25, 2010

(65) Prior Publication Data
US 2012/0121461 A1    May 17, 2012

(30) Foreign Application Priority Data

May 22, 2009    (GB) .................................. 0908849.3

(51) Int. Cl.
| | |
|---|---|
| *A61K 51/00* | (2006.01) |
| *B08B 7/00* | (2006.01) |
| *B08B 9/00* | (2006.01) |
| *B08B 3/00* | (2006.01) |
| *A61L 2/00* | (2006.01) |
| *A01N 25/16* | (2006.01) |
| *A01N 59/00* | (2006.01) |
| *A61L 2/22* | (2006.01) |
| *C01B 11/02* | (2006.01) |

(52) U.S. Cl.
CPC ................ *A61L 2/0082* (2013.01); *A01N 25/16* (2013.01); *A01N 59/00* (2013.01); *A61L 2/22* (2013.01); *C01B 11/024* (2013.01)

(58) Field of Classification Search
CPC ..... A01N 1/0215; A01N 25/04; A61K 8/046; A61K 8/315; A61L 2/00; A61L 9/012
USPC ........ 422/1, 28, 37; 134/6, 22.1, 26, 84, 94.1, 134/99.1; 424/1.13
See application file for complete search history.

(56) References Cited

U.S. PATENT DOCUMENTS 5,616,347 A    4/1997   Alliger et al.
2005/0215459 A1*   9/2005   Policicchio et al. .......... 510/438

FOREIGN PATENT DOCUMENTS

| GB | 2 422 545 A | 8/2006 | |
|---|---|---|---|
| GB | WO 2006/079822 A1 * | 8/2006 | ................ A61L 2/18 |

(Continued)

OTHER PUBLICATIONS

Form PCT/ISA/210 for corresponding International Application PCT/GB2010/050525.

(Continued)

*Primary Examiner* — Monzer R Chorbaji
(74) *Attorney, Agent, or Firm* — Merchant & Gould P.C.

(57) ABSTRACT

A hand sanitizer (2) comprises: (a) a first part comprising a chlorite in an alcoholic medium having a first foam promoter dissolved therein and contained in a first foam dispenser (4) whereby it is dispensed as a first foam; and (b) a second part which comprises an acid in an alcoholic medium which has a second foam promoter dissolved therein and which is contained in a second foam dispenser (6) whereby it is dispensed as a second foam; wherein the chlorite and the acid will react to provide chlorine dioxide when the first foam is mixed with the second foam; and wherein a mixture (18) of equal quantities of the first part and the second part contains at least 50% alcohol by weight.

8 Claims, 2 Drawing Sheets

(56) References Cited

FOREIGN PATENT DOCUMENTS

WO  WO 2005/011756  A1  2/2005
WO  WO 2006/079822  A1  8/2006

OTHER PUBLICATIONS

Form PCT/ISA/237 for corresponding International Application PCT/GB2010/050525.

* cited by examiner

HAND SANITIZER

This application is a National Stage Application of PCT/GB2010/050525, filed 29 Mar. 2010, which claims benefit of Serial No. 0908849.3, filed 22 May 2009 in the United Kingdom and which applications are incorporated herein by reference. To the extent appropriate, a claim of priority is made to each of the above disclosed applications.

BACKGROUND

The present invention relates to a hand sanitizer.

The rise of hospital-acquired infections such as MRSA and *Clostridium difficile* has emphasized the need for cleanliness. In particular, effective hand sanitizing is needed for people working in a clinical environment.

SUMMARY OF THE INVENTION

Aspects of the invention are specified in the independent claims. Preferred features are specified in the dependent claims.

The invention provides the benefits of an antibacterial alcohol hand wash and sanitizer with the sporicidal properties of chlorine dioxide ($ClO_2$).

The term "alcoholic medium" is used herein to refer to a fluid containing alcohol, typically an aqueous solution of an alcohol. The alcohol may be ethanol, isopropanol, n-propanol or a mixture of these. In one embodiment the alcohol is or contains 3-methoxy-3-methylbutan-1-ol (MMB) which we have found to provide fast drying times and improved skin feel compared to ethanol.

We have surprisingly found that producing $ClO_2$ in an the presence of a substantial quantity of an alcohol does not noticeably result in disagreeable oxidized products of the alcohol, such as acetaldehyde or acetic acid from ethanol. Without wishing to be bound by theory, we believe that the short time during which the $ClO_2$ is in contact with the alcohol when the foams are mixed does not allow oxidation of the alcohol to a level where the smell of oxidized product is noticeable. Moreover, we have surprisingly found that sodium chlorite is stable in an alcoholic medium for extended periods, despite its being an oxidizing agent.

The foam dispensers may be provided in a common housing and dispensed using a common actuator, for example as described in WO 2006/079822, the contents of which are hereby incorporated by reference in their entirety.

BRIEF DESCRIPTION OF THE DRAWINGS

The invention will now be further described, by way of example only, with reference to the following drawings in which.

DETAILED DESCRIPTION

Figure 1:
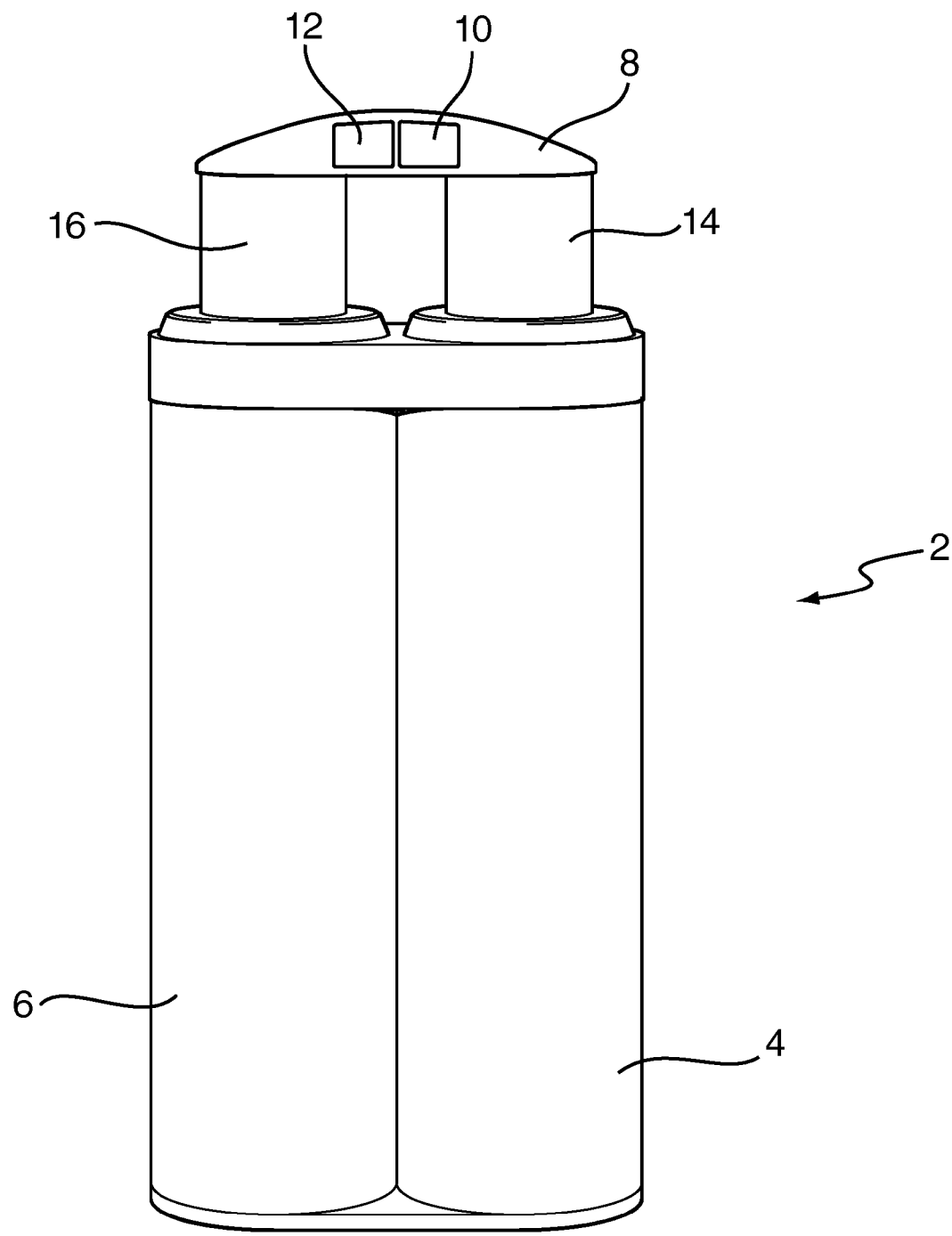
FIG. 1 shows a hand sanitizer in accordance with an embodiment of the invention.

In this specification, all parts are by weight unless otherwise indicated.

The hand sanitizer 2 in this example uses a Dual Foamer foam dispenser from Airspray International BV. The hand sanitizer 2 has a first dispenser chamber 4 clipped to a second dispenser chamber 6. The chambers 4, 6 are part of two small foam pump systems which dispense their contents as foams when respective piston members 14, 16 are depressed. Operation of a single actuator 8 depresses both piston members 14, 16, causing a volume of liquid (in this example, 0.8 ml) to be pumped from each chamber 4, 6 simultaneously and combined with air to form a foam. The liquid from chamber 4 is turned into a first foam and the liquid from chamber 6 is turned into a second foam. The first and second foams are dispensed via respective separate nozzle orifices 10, 12 in the actuator 8.

The first dispenser chamber 4 contains a first part comprising a chlorite in an aqueous medium having a first foam promoter dissolved therein and contained in a first foam dispenser whereby it is dispensed as a first foam. Exemplary formulations of the first part are set out in Table 1A and Table 2A.

The second dispenser chamber 6 contains a second part comprising an acid in an alcoholic medium which has a second foam promoter dissolved therein and which is contained in a second foam dispenser whereby it is dispensed as a second foam. Exemplary formulations of the second part are set out in Table 1B and Table 2B.

TABLE 1A

| First Part | | % |
|---|---|---|
| 1 | Demineralized water | Balance |
| 2 | Sodium chlorite solution | 0.5 |
| 3 | Surfactant (dimethicone Copolyol) | 0.5 |
| 4 | Ethanol-B | 80 |
| 5 | Hydroxyethylcellulose | 0.25 |

TABLE 1B

| Second Part | | % |
|---|---|---|
| 1 | Demineralized water | Balance |
| 2 | Ethanol-B | 80 |
| 3 | Citric acid (ANH) | 1 |
| 4 | Sorbic acid | 0.01 |
| 5 | Boric acid | 0.01 |
| 6 | Glycerine (veg) | 0.5 |
| 7 | Sodium benzoate | 0.2 |
| 8 | Surfactant (dimethicone copolyol) | 0.5 |
| 9 | Hydroxyethylcellulose | 0.25 |
| 10 | Sodium acetate | 0.2 |

In both the first part and the second part, dimethicone copolyol surfactant is used as a foam promoter. In other embodiments, we have found that a surfactant comprising a mixture of equal parts of dimethicone copolyol, polydimethylsiloxane diquat, alkylamino carboxylate and alkylbetaine, gives good foam stability with both aqueous and alcoholic media.

TABLE 2A

| First Part | | % |
|---|---|---|
| 1 | Demineralized water | Balance |
| 2 | Sodium chlorite solution | 0.5 |
| 3 | Surfactant (dimethicone Copolyol) | 0.5 |
| 4 | Ethanol-B | 30 |
| 5 | Hydroxyethylcellulose | 0.25 |

TABLE 2B

| Second Part | | % |
|---|---|---|
| 1 | Demineralized water | Balance |
| 2 | Ethanol-B | 70 |

TABLE 2B-continued

| Second Part | | % |
|---|---|---|
| 3 | Citric acid (ANH) | 1 |
| 4 | Sorbic acid | 0.01 |
| 5 | Boric acid | 0.01 |
| 6 | Glycerine (veg) | 0.5 |
| 7 | Sodium benzoate | 0.2 |
| 8 | Surfactant (dimethicone copolyol) | 0.5 |
| 9 | Hydroxyethylcellulose | 0.25 |
| 10 | Sodium acetate | 0.2 |

Figure 2:
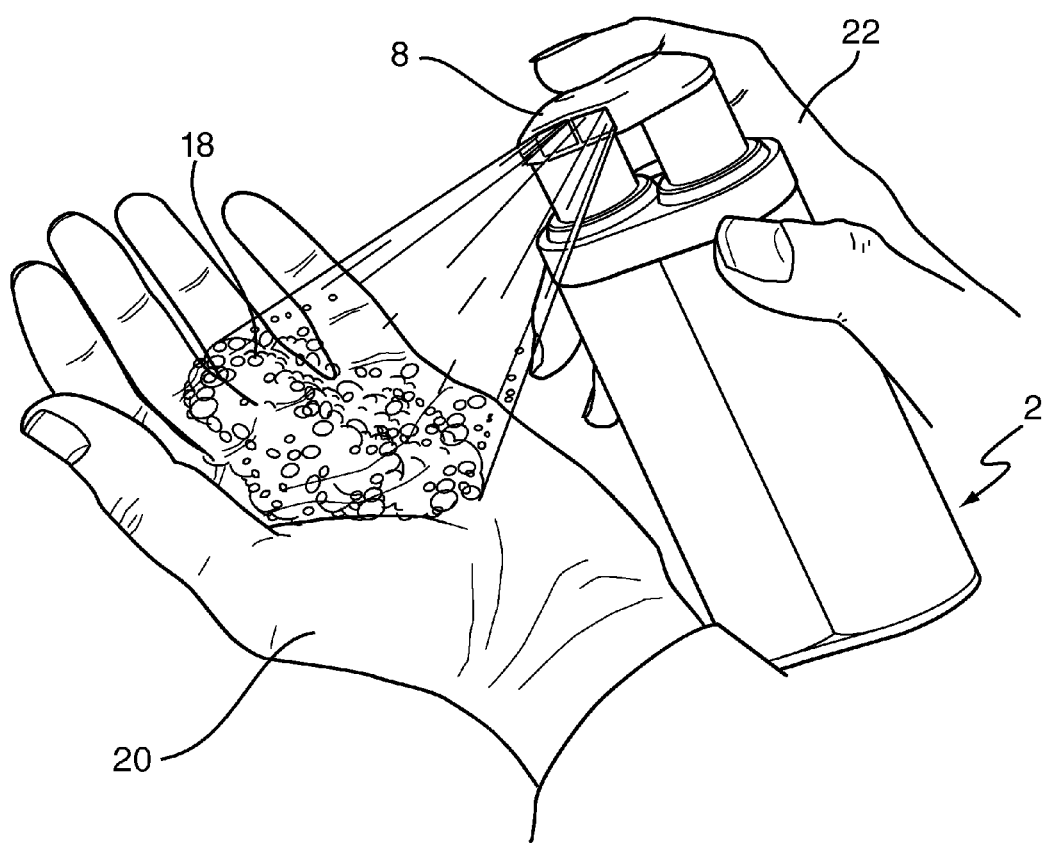
FIG. 2 shows the hand sanitizer of FIG. 1 in use.

Referring now to FIG. 2, the foam from each nozzle is sprayed onto a user's hand 20 by the action of a user's finger 22 on the actuator 8. The foams mix to provide a sterilizing foam composition 18 containing ethanol and $ClO_2$. The user rubs both hands together to mix the foams thoroughly and cover his hands with the sterilizing foam composition 18.

Antibiotics, antivirals, or other antimicrobial agents may optionally be incorporated in either or both of the first part and the second part. Suitable agents will be well known to those of ordinary skill in the art. Examples include cationics, amphoterics and phenolics.

After the user's hands have been thoroughly sanitized by covering and rubbing with the foam mixture 18, the user may rinse off the mixture 18. However, the alcohol content makes the foam mixture quite volatile and the user may choose simply to allow his hands to dry by evaporation.

The embodiment of Table 1 provides foams which, contain 80% alcohol and, when combined, chlorine dioxide, which we have found provides excellent sterilizing properties when used as a hand sanitizer, being more effective than conventional alcohol hand sanitizers or chlorine dioxide hand sanitizers alone.

The embodiment of Tables 2A and 2B has 30% alcohol in the First Part, and 70% alcohol in the second part. When dispensed as foams and mixed, in equal parts, the combined foam has 50% alcohol, and also provides effective hand sterilization.

Humectants, moisturizers and fragrances may optionally be included in the first part or (preferably) the second part, as is well known in the art per se.

Corrosion inhibitors may be included in the first part and/or the second part, for improved packaging and protection of the dispenser.

We have found that in order to achieve an alcoholic foam with suitable stability and 'quick-break' properties, incorporation of a thickener or film former (hydroxyethylcellulose in the examples of Tables 1 and 2) is desirable. The optimum range for the film former is 0.01-1%, preferably 0.1-0.25%. Limiting the concentration of film former to about 0.25% helps to reduce unwanted residue when the hand sanitizer is used without rinsing.

TABLE 3A

| | First Part | |
|---|---|---|
| | Material | % |
| | Demineralized Water | Balance |
| | Sodium chlorite | 0.50 |
| * | Surfactant | 0.50 |
| *** | Alcohol | 80.00 |
| ** | Film formers | 0.25 |

TABLE 3B

| | Second Part | |
|---|---|---|
| | Material | % |
| | Demineralized Water | Balance |
| | Sodium chlorite | 0.50 |
| * | Surfactant | 0.50 |
| *** | Alcohol | 30.00 |
| ** | Film formers | 0.25 |

TABLE 4A

| * | Surfactant combination of: |
| | Dimethicone Copolyol |
| | Polydimethylsiloxane Diquat |
| | Alkylamino Carboxylate + Alkylbetaine |
| ** | Film formers - see list below |
| *** | Ethanol, isopropanol, n-propanol |

| | First Part | |
|---|---|---|
| | Component | % |
| | Demineralized Water | Balance |
| *** | Alcohol | 80.00 |
| | Citric Acid | 1.00 |
| | Sorbic Acid | 0.01 |
| | Boric Acid | 0.01 |
| | Glycerine | 0.50 |
| | Sodium Benzoate | 0.20 |
| * | Surfactant | 0.50 |
| ** | Film formers | 0.25 |
| | Sodium Acetate | 0.20 |

TABLE 4B

| | Second Part | |
|---|---|---|
| | Material | % |
| | Demineralized Water | Balance |
| *** | Alcohol | 70.00 |
| | Citric Acid | 1.00 |
| | Sorbic Acid | 0.01 |
| | Boric Acid | 0.01 |
| | Glycerine | 0.50 |
| | Sodium Benzoate | 0.20 |
| * | Surfactant | 0.50 |
| ** | Film formers | 0.25 |
| | Sodium Acetate | 0.20 |

Suitable film formers include: alginates, alkyl and hydroxyalkylcellulose, carboxymethylcellulose, carrageenan, guar gum, gum agar, gum Arabic, gum ghatti, gum karaya, gum tragacanth, hydroxyethylcellulose, hydroxypropylcellulose, locust bean gum, pectins, polyacrylamide, poly (acrylic acid) and its homologs, poly(ethylene glycol), poly (ethylene oxide), poly(vinyl alcohol), poly(vinyl pyrrolidone) starch and its modifications, tamarind gum, xanthan gum.

It will be appreciated that alternative film formers well known per se to those skilled in the art may be used provided that they are soluble in the alcoholic medium. Moreover, alternative surfactants may be used, notably surfactants which aid in foam stabilization. Non-limiting examples include: carboxylic acid salts, sulphonic acid salts (for example linear or non-linear alkyl benezesulphonates, methyl ester-α-sulphonates, α-olefin sulphonates), sulphuric acid ester salts, alkyl sulphates, alkyl ethoxylate sulphates, alkyl sulphate triethanolamines, diethanolamide, alkyl ethoxylates, alkyl phenyl ethoxylates, alkyl trimethylammonium salts, dialkyl dimethylammonium chlorides, alkyl pyridinium chlorides, alkyl carboxybetaines, phosphoric and polyphosphoric acid esters, fluorinated anionics, long chain amines and their salts, acylated diamines and polymines and their salts, quaternary ammonium salts, polyoxyethylenated (POE) long-chain amines, amine oxides, POE alklyphenols, alkylphenol "ethoxylates", POE straight-chain alcohols, alcohol "ethoxylates", POE polyoxypropylene glycols, POE mercaptans, long-chain carboxylic acid esters, alkanolamine "condensates", alkanolamides, tertiary acetylenic glycols and their "ethoxylates" POE silicones, N-alkylpyrrolidones, alkylpolyglycosides, pH-sensitive zwitterionics, pH-insensitive zwitterionics, α-sulphofatty acid methyl esters (SME), acylated aminoacids, N-acyl L-glutamates, N-acyl glycinates, N-acyl DL-alananinates, other acylated aminoacids, Nopol alkoxylates.

In another embodiment, we have found that use of MMB as some or all of the alcohol component can provide the benefits of fast drying and greatly improved skin feel compared to ethanol. MMB also has the benefit over ethanol that it is substantially non-flammable. Pure MMB has a flash point of 68° C. measured by Tag Closed Cup, while a mixture of MMB and 10% or more water has no flash point. MMB is considered to be extremely safe, having no R and S phrases and Occupational Exposure Limit.

Table 5 summarises comparative drying speeds of mixtures of MMB and water, and mixtures of ethanol and water. In each case, a 0.1 ml sample was visually assessed for speed of drying. Rates of evaporation were determined by placing a sample onto a standard filter paper and measuring the time for complete evaporation. The time for diethyl ether evaporation is taken as unity, and the quoted numbers for each sample are expressed relative to diethyl ether.

TABLE 5

| Demin. Water (D) | 10% Ethanol in D. | 50% Ethanol in D. | 10% MMB in D. | 50% MMB in D. |
|---|---|---|---|---|
| 77 | 21 | 12 | 24 | 14 |

The above demonstrates a similar evaporation rate for comparable solutions of ethanol in water and MMB in water. Qualitative testing demonstrated a greatly improved skin feel of MMB over ethanol.

The invention claimed is:

1. A hand sanitizer composition comprising:
   (a) a first part comprising a chlorite in a first alcoholic medium having a first foam promoter dissolved therein and contained in a first foam dispenser wherein the first foam dispenser is constructed to dispense the first part as a first foam; and
   (b) a second part which comprises an acid in a second alcoholic medium which has a second foam promoter dissolved therein and which is contained in a second foam dispenser wherein the second foam dispenser is constructed to dispense the second part as a second foam;
   wherein the chlorite and the acid will react to provide chlorine dioxide when the first foam is mixed with the second foam; and wherein the first alcoholic medium is provided in the first part and the second alcoholic medium is provided in the second part in amounts sufficient so that a combination of equal quantities of the first part and the second part contains at least 50% by weight ethanol, isopropanol, n-propanol, or a mixture thereof.

2. A hand sanitizer composition according to claim 1, wherein the alcohol is present in a concentration of from 50-80% by weight when equal quantities of the first part and the second part are mixed.

3. A hand sanitizer composition according to claim 1, wherein the first part and the second part each further comprises from 0.01 to 1% by weight of a thickener or film former.

4. A hand sanitizer composition according to claim 3, wherein the thickener or film former is present in a concentration of from 0.1 to 0.25% by weight.

5. A hand sanitizer composition according to claim 1, further comprising 3-methoxy-3-methylbutan-1-ol (MMB).

6. A hand sanitizer composition according to claim 1, wherein the foam promoter is dimethicone copolyol, polydimethylsiloxane diquat, alkylamino carboxylate and alkylbetaine or a mixture of any or all of the aforementioned components.

7. A method of sanitizing hands, comprising dispensing a hand sanitizer composition according to claim 1, to form the first foam and the second foam on a user's hands, and rubbing the user's hands together to mix the first foam and the second foam to form a mixed foam, and covering the user's hands with the mixed foam.

8. A hand sanitizer composition comprising:
   (a) a first part comprising a chlorite in a first alcoholic medium having a first foam promoter dissolved therein and contained in a first foam dispenser wherein the first foam dispenser is constructed to dispense the first part as a first foam; and
   (b) a second part which comprises an acid in a second alcoholic medium which has a second foam promoter dissolved therein and which is contained in a second foam dispenser wherein the second foam dispenser is constructed to dispense the second part as a second foam;
   wherein the chlorite and the acid will react to provide chlorine dioxide when the first foam is mixed with the second foam; and wherein the first alcoholic medium is provided in the first part and the second alcoholic medium is provided in the second part in amounts sufficient so that a combination of equal quantities of the first part and the second part contains at least 50% alcohol by weight, wherein substantially all of the alcohol is 3-methoxy-3-methylbutan-1-ol.

* * * * *